United States Patent
Krueger et al.

(10) Patent No.: US 8,828,270 B2
(45) Date of Patent: Sep. 9, 2014

(54) COMPOSITION COMPRISING AN ALPHA-CYCLODEXTRIN-CHLORINE DIOXIDE COMPLEX AND AN INERT SUBSTANCE, AND ALSO METHOD FOR PRODUCTION THEREOF

(75) Inventors: Benno Krueger, Burghausen (DE); Gerald Fleischmann, Burghausen (DE); Stefan Neumann, Kastl (DE)

(73) Assignee: Wacker Chemie AG, Munich (DE)

( * ) Notice: Subject to any disclaimer, the term of this patent is extended or adjusted under 35 U.S.C. 154(b) by 216 days.

(21) Appl. No.: 13/425,553

(22) Filed: Mar. 21, 2012

(65) Prior Publication Data

US 2012/0259108 A1 Oct. 11, 2012

(30) Foreign Application Priority Data

Apr. 8, 2011 (DE) .......................... 10 2011 007 057

(51) Int. Cl.
| | | |
|---|---|---|
| *C08B 11/02* | (2006.01) | |
| *A01N 59/00* | (2006.01) | |
| *A01N 25/08* | (2006.01) | |
| *A01N 25/10* | (2006.01) | |
| *C01B 11/02* | (2006.01) | |

(52) U.S. Cl.
CPC ................ *C01B 11/022* (2013.01); *A01N 25/08* (2013.01); *A01N 25/10* (2013.01); *A01N 59/00* (2013.01)
USPC ........ 252/187.21; 422/37; 423/477; 424/661; 514/778

(58) Field of Classification Search
None
See application file for complete search history.

(56) References Cited

U.S. PATENT DOCUMENTS 4,689,169 A * 8/1987 Mason et al. ............ 252/186.24

FOREIGN PATENT DOCUMENTS

| CN | 101703071 A | 5/2010 |
|---|---|---|
| JP | 60161307 | 8/1985 |
| JP | 63246304 | 10/1988 |
| JP | 6471804 | 3/1989 |
| JP | 6228469 | 8/1994 |
| JP | 2006204445 | 8/2006 |
| JP | 2010536861 | 12/2010 |
| WO | 2009026014 A1 | 2/2009 |

OTHER PUBLICATIONS

English language abstract for JP2006-204445, (2006).
English language abstract for JP63-246304, (1988).
English language abstract for JP64-71804, (1989).
English language abstract for JP60-161307, (1985).
English language abstract for JP6-228469, (1994).
English abstract of CN101703071, (2010).

* cited by examiner

*Primary Examiner* — Leigh Maier

(74) *Attorney, Agent, or Firm* — Caesar, Rivise, Bernstein, Cohen & Pokotilow, Ltd.

(57) ABSTRACT

The invention relates to a safely handleable and transportable composition including an alpha-cyclodextrin-chlorine dioxide complex and an inert substance, and also a method for production thereof.

8 Claims, No Drawings

COMPOSITION COMPRISING AN ALPHA-CYCLODEXTRIN-CHLORINE DIOXIDE COMPLEX AND AN INERT SUBSTANCE, AND ALSO METHOD FOR PRODUCTION THEREOF

BACKGROUND OF THE INVENTION

The invention relates to a safely handleable and transportable composition comprising an alpha-cyclodextrin-chlorine dioxide complex and an inert substance, and also method for production thereof.

An alpha-cyclodextrin-chlorine dioxide complex is a self-decomposing product having a highly exothermic decomposition energy (>1005 J/g) and a low decomposition temperature. Buildup of heat during storage or transport can cause fire or exothermic decomposition. The transport of the complex is only permissible 15° C. below the "self-accelerating decomposition temperature" (SADT) which is <35° C. for the alpha-cyclodextrin-chlorine dioxide complex. The complex is therefore unsuitable for practical use (transport, storage etc.).

Production of an alpha-cyclodextrin-chlorine dioxide complex and also conditions for storage and stability are known, for example, from WO/2009026014. There, it is also described that the complex is stable or storable only at low temperatures. An alpha-cyclodextrin-chlorine dioxide complex is therefore, on an industrial scale, neither safely nor economically producible and also its in itself desirable use for many applications as are likewise described in WO/2009026014, owing to its highly exothermic decomposition energy and the low temperature thereof at which the decomposition starts (hereinafter also named onset temperature), is virtually impossible.

The object of the invention was to provide a composition containing an alpha-cyclodextrin-chlorine dioxide complex which is safely handleable and transportable.

DESCRIPTION OF THE INVENTION

This object is achieved by a composition comprising an alpha-cyclodextrin-chlorine dioxide complex and also an inert substance.

An inert substance, in the context of the present application, is taken to mean a substance which reacts neither with chlorine dioxide nor with cyclodextrin, nor promotes an exothermal decomposition of the alpha-cyclodextrin-chlorine dioxide complex. Addition of the inert substance to the alpha-cyclodextrin-chlorine dioxide complex effects a reduction of the heat of decomposition, an increase in the temperature of the start of decomposition, a reduction of the heat of self-decomposition by endothermic reaction and a reduction of the risk of fire of the complex in the composition.

Preferably, the inert substance is a substance from the group silicic acid, silica gel, alkaline earth metal salt of silicic acid, alkaline earth metal salt of sulfuric acid, alkaline earth metal salt of phosphoric acid, alkaline earth metal salt of hydrofluoric acid, alkaline earth metal salt of carbonic acid, oxide of aluminum, oxide of magnesium, oxide of silicon, oligo- or polysaccharides having a water solubility<50 g/l (at 25° C.), vinyl alcohol copolymers and milled natural mineral.

As milled natural mineral, preferably alkaline earth metal sulfates, dolomite, limestone, talc, magnesite, diatomaceous earth or any desired mixture of these minerals in milled form is used.

The milled material is preferably milled to be sufficiently fine that it is suspendable and transportable in water.

Particularly preferably, the inert substance is silica gel, silicic acid, diatomaceous earth, oligo- or polysaccharide having a water solubility<50 g/l (at 25° C.) or vinyl alcohol copolymer.

Preferably, the preparation according to the invention contains 5 to 80% by weight, based on the total weight of the composition, of alpha-cyclodextrin-chlorine dioxide complex and 20 to 95% by weight, based on the total weight of the composition, of inert substance.

Preferably, the composition according to the invention comprises the alpha-cyclodextrin-chlorine dioxide complex and the inert substance.

The alpha-cyclodextrin-chlorine dioxide complex inert substance mixture can be produced in that an alpha-cyclodextrin-chlorine dioxide complex is mixed with at least one inert substance.

The alpha-cyclodextrin-chlorine dioxide complex inert substance mixture is preferably produced in that an aqueous alpha-cyclodextrin solution and an inert substance are mixed and chlorine dioxide is introduced into this mixture, wherein the composition comprising an alpha-cyclodextrin-chlorine dioxide complex and an inert substance precipitates out, and this composition is separated off. In this method, the alpha-cyclodextrin-chlorine dioxide complex is produced in the presence of a suspension of the inert substance, in such a manner that the alpha-cyclodextrin-chlorine dioxide complex is formed homogeneously distributed in the inert substance suspension and is already isolated as a homogeneous mixture with the inert substance. In the case of the inert substance alpha-cyclodextrin-chlorine dioxide complex thus obtained, the heat of decomposition of the composition according to the invention is surprisingly markedly lowered compared with the pure alpha-cyclodextrin-chlorine dioxide complex. Since, at the same time, the onset temperature rises, production, handling, storage and transport of the composition according to the invention are safely possible. In particular, the hazard-free production and recovery of the composition according to the invention is possible by this method.

The composition according to the invention is preferably produced at a temperature of 0 to 30° C., more preferably 0° C. to 20° C., over a period of 1 to 10 min, particularly preferably 1 to 5 min, and/or at a pH of 3.0 to 9.0.

The composition is generally formed at atmospheric pressure. Preferably, complexation takes place under a protective gas atmosphere (nitrogen or argon) and also in the absence of daylight.

A suspension thus formed can be used directly, but can also be isolated and prepared by filtration, centrifugation, drying, milling, sieving, sifting, granulation, tableting, or further formulated in a use-specific manner.

The composition according to the invention can be used for all purposes already mentioned in WO/2009026014, there, in particular on p. 11.

The examples hereinafter serve for further illustration of the invention.

Comparative Example 1

Production of a $ClO_2$-alpha-cyclodextrin complex and determination of the thermal stability thereof.

Chlorine dioxide and the $ClO_2$ complex with alpha-cyclodextrin (hereinafter abbreviated as: $ClO_2$ complex) were produced in a similar manner to WO/2009026014:

A 2-4 molar excess of chlorine dioxide was introduced into an 8.3% strength aqueous alpha-cyclodextrin solution at room temperature, which, in the context of the present application, is to be taken to mean 23° C. The alpha-cyclodextrinchlorine dioxide complex was virtually water-insoluble and therefore precipitated out. The complex was isolated by filtering off with suction, washing with acetone and drying in vacuum at temperatures of a maximum of 30° C., typically at yields of 50-60% (based on the amount of cyclodextrin used).

Small amounts (<1 kg) of this complex may be stored at low temperature (freezer cabinet; −18° C.) stable up to 3 months. At elevated temperatures (30-50° C.), even after a few days, complete decomposition with carbonization phenomena was to be observed.

The thermal stability of the samples under study was studied using dynamic difference calorimetry (DSC). As sample container, a pressure-resistant steel crucible having a glass insert (DSC crucible) was used, which ensures that no evaporation losses are possible. All measurements were performed in the DSC crucible under an $N_2$ atmosphere.

TABLE 1

Results of the DSC studies

| No | Composition/mass ratios % by weight | Range ° C. | −ΔH$_r$ kJ kg$^{-1}$ K$^{-1}$ | ΔT$_{ad}$ ° C. |
|---|---|---|---|---|
| 1 | $ClO_2$ complex = 100 | 61-243 | 1005 | 503 |

Abbreviations:
Range In this temperature range, a decomposition reaction was observed. The left-hand boundary corresponds to the onset temperature of decomposition.
−ΔHr Decomposition enthalpy in kJ per kg of mixture.
ΔTad Adiabatic temperature increase Examples 1-5

Production of Alpha-Cyclodextrin-$ClO_2$-Inert Substance Preparations and Determination of Thermal Stability Thereof Different amounts (see tab. 2) of water-insoluble inorganic inert substances (see tab. 2) were added to 718 g of an 8% strength aqueous alpha-cyclodextrin solution. Chlorine dioxide in four-fold excess was introduced into the resultant suspension with cooling. After 90 minutes, the metering was ended. The alpha-cyclodextrin-chlorine dioxide complex formed in the presence of the inert substance was filtered off by suction together with the inert substance as a visually homogeneous mixture, washed with acetone and dried in a vacuum at room temperature.

The thermal stability of the samples under study was studied using dynamic differential calorimetry (DSC) in a similar manner to comparative example 1.

TABLE 2

$ClO_2$ complex formation in the presence of inert fillers

| No | Composition/mass ratios % by weight | Range ° C. | −ΔH$_r$ kJ kg$^{-1}$ K$^{-1}$ | ΔT$_{ad}$ ° C. |
|---|---|---|---|---|
| 1 | Silica gel:$ClO_2$ complex = 61.4:38.6 | 83-145 180-252 259-373 | 146 162 209 | 82 90 117 |
| 2 | Silica gel:$ClO_2$ complex = 67.6:32.4 | 83-147 158-247 | 112 167 | 63 93 |
| 3 | Talc:$ClO_2$ complex = 47.1:52.9 | 83-150 158-253 268-349 | 244 288 47 | 136 160 27 |

TABLE 2-continued $ClO_2$ complex formation in the presence of inert fillers

| No | Composition/mass ratios % by weight | Range ° C. | −ΔH$_r$ kJ kg$^{-1}$ K$^{-1}$ | ΔT$_{ad}$ ° C. |
|---|---|---|---|---|
| 4 | Talc:$ClO_2$ complex = 37.9:62.1 | 86-164 166-236 | 319 244 | 178 136 |
| 5 | $BaSO_4$:$ClO_2$ complex = 57.7:42.3 | 67-149 164-255 300-360 | 192 129 38 | 96 65 19 |

Abbreviations:
Range In this temperature range, a decomposition reaction was observed. The left-hand boundary corresponds to the onset temperature of decomposition.
−ΔHr Decomposition enthalpy in kJ per kg of mixture.
ΔTad Adiabatic temperature increase

What is claimed is:

1. A composition comprising:
   5 to 80% by weight, based on a total weight of the composition, of an alpha-cyclodextrin-chlorine dioxide complex; and
   20 to 95% by weight, based on the total weight of the composition, of at least one inert substance selected from the group consisting of silicic acid, silica gel, alkaline earth metal salt of silicic acid, alkaline earth metal salt of sulfuric acid, alkaline earth metal salt of phosphoric acid, alkaline earth metal salt of hydrofluoric acid, alkaline earth metal salt of carbonic acid, oxide of aluminum, oxide of magnesium, oxide of silicon, oligo- or polysaccharide having a water solubility <50 g/l (at 25° C.), vinyl alcohol copolymer and milled natural mineral, wherein the milled natural mineral is a member selected from the group consisting of an alkaline earth metal sulfate, dolomite, limestone, talc, magnesite, diatomaceous earth and mixtures thereof.

2. The composition as claimed in claim 1, consisting of the alpha-cyclodextrin-chlorine dioxide complex and the at least one inert substance.

3. A method for producing a composition as claimed in claim 1, wherein the alpha-cyclodextrin-chlorine dioxide complex is mixed with the at least one inert substance.

4. A method for producing a composition as claimed in claim 2, wherein the alpha-cyclodextrin-chlorine dioxide complex is mixed with the at least one inert substance.

5. A method for producing a composition comprising an alpha-cyclodextrin-chlorine dioxide complex and at least one inert substance, said method comprising:
   mixing an aqueous alpha-cyclodextrin solution and at least one inert substance to provide a mixture;
   introducing chlorine dioxide into the mixture so as to precipitate the composition from the mixture; and
   separating off the composition precipitated from the mixture.

6. The method of claim 5, wherein the composition consists of the alpha-cyclodextrin chlorine dioxide complex and the at least one inert substance.

7. The method of claim 5, wherein: (a) the alpha-cyclodextrin-chlorine dioxide complex constitutes 5 to 80% by weight of a total weight of the composition; (b) the at least one inert substance constitutes 20 to 95% by weight of the total weight of the composition and is a member selected from the group consisting of silicic acid, silica gel, alkaline earth metal salt of silicic acid, alkaline earth metal salt of sulfuric acid, alkaline earth metal salt of phosphoric acid, alkaline earth metal salt of hydrofluoric acid, alkaline earth metal salt of carbonic acid, oxide of aluminum, oxide of magnesium, oxide of silicon, oligo- or polysaccharide having a water solubility <50 g/l (at 25° C.), vinyl alcohol copolymer and milled natural mineral;

and (c) the milled natural mineral is a member selected from the group consisting of an alkaline earth metal sulfate, dolomite, limestone, talc, magnesite, diatomaceous earth and mixtures thereof.

8. The method of claim 7, wherein the composition consists of the alpha-cyclodextrin chlorine dioxide complex and the at least one inert substance.

\* \* \* \* \*